United States Patent
Reyes et al.

(10) Patent No.: US 11,318,295 B2
(45) Date of Patent: May 3, 2022

(54) HVAD RINSE VIA A NON-UNIFORM THRUST BEARING GAP

(71) Applicant: HeartWare, Inc., Miami Lakes, FL (US)

(72) Inventors: Carlos Reyes, Davie, FL (US); Justin Wolman, Aventura, FL (US)

(73) Assignee: HeartWare, Inc., Miami Lakes, FL (US)

( * ) Notice: Subject to any disclaimer, the term of this patent is extended or adjusted under 35 U.S.C. 154(b) by 184 days.

(21) Appl. No.: 16/778,658

(22) Filed: Jan. 31, 2020

(65) Prior Publication Data

US 2020/0276368 A1    Sep. 3, 2020

Related U.S. Application Data

(60) Provisional application No. 62/811,618, filed on Feb. 28, 2019.

(51) Int. Cl.
*A61M 60/824* (2021.01)
*A61M 60/148* (2021.01)
*A61M 60/405* (2021.01)

(52) U.S. Cl.
CPC ........ *A61M 60/824* (2021.01); *A61M 60/148* (2021.01); *A61M 60/405* (2021.01); *A61M 2205/04* (2013.01); *A61M 2205/103* (2013.01)

(58) Field of Classification Search
CPC .............. A61M 60/824; A61M 60/405; A61M 60/148; A61M 2205/04; A61M 2205/103
See application file for complete search history.

(56) References Cited

U.S. PATENT DOCUMENTS

| | | | |
|---|---|---|---|
| 6,183,486 B1 | 2/2001 | Snow et al. | |
| 6,688,861 B2 | 2/2004 | Wampler | |
| 7,575,423 B2 | 8/2009 | Wampler | |
| 7,976,271 B2 | 7/2011 | LaRose et al. | |
| 8,007,254 B2 * | 8/2011 | LaRose ............... | A61M 60/135 417/356 |
| 8,419,609 B2 | 4/2013 | Shambaugh, Jr. et al. | |

(Continued)

FOREIGN PATENT DOCUMENTS

| | | |
|---|---|---|
| JP | 2005121157 A | 5/2005 |
| WO | 2014000753 A1 | 1/2014 |

OTHER PUBLICATIONS

PCT/US2020/017461, PCT International Search Report and Written Opinion, dated Jun. 9, 2020, 9pages.

(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

A blood pump having a housing including an inlet element. The inlet element has a proximal portion sized to be received within at least a portion of a heart of a patient and defines a major longitudinal axis. A rotor is configured to rotate within the housing about the major longitudinal axis and impel blood from heart. At least one stator is disposed within the housing and positioned within the housing at least one from the group consisting of upstream and downstream from the rotor. During operation of the blood pump the rotor is maintained at an oblique angle with respect to the major longitudinal axis.

20 Claims, 4 Drawing Sheets

(56) References Cited

U.S. PATENT DOCUMENTS

| | | | |
|---|---|---|---|
| 2002/0031436 A1* | 3/2002 | Maeda | F04D 13/027 417/420 |
| 2009/0123309 A1* | 5/2009 | Hilber | F04B 19/006 417/417 |
| 2016/0235898 A1* | 8/2016 | Yanai | F04D 13/0666 |
| 2016/0361536 A1 | 12/2016 | Grubac et al. | |
| 2018/0071543 A1 | 3/2018 | Taff et al. | |
| 2018/0178023 A1 | 6/2018 | Becklund et al. | |
| 2018/0303989 A1 | 10/2018 | Casas | |
| 2019/0038820 A1* | 2/2019 | Granegger | A61M 60/50 |
| 2019/0054222 A1* | 2/2019 | Reyes | A61M 5/14276 |
| 2019/0111194 A1* | 4/2019 | Reyes | A61M 60/857 |
| 2019/0167874 A1* | 6/2019 | Egler | A61M 60/148 |

OTHER PUBLICATIONS

Medtronic, Micra Transcatheter Pacing System. https://www.medtronic.com/us-en/healthcare-professionals/products/cardiac-rhythm/pacemakers/micra-pacing-system.html, 10 pages.

* cited by examiner

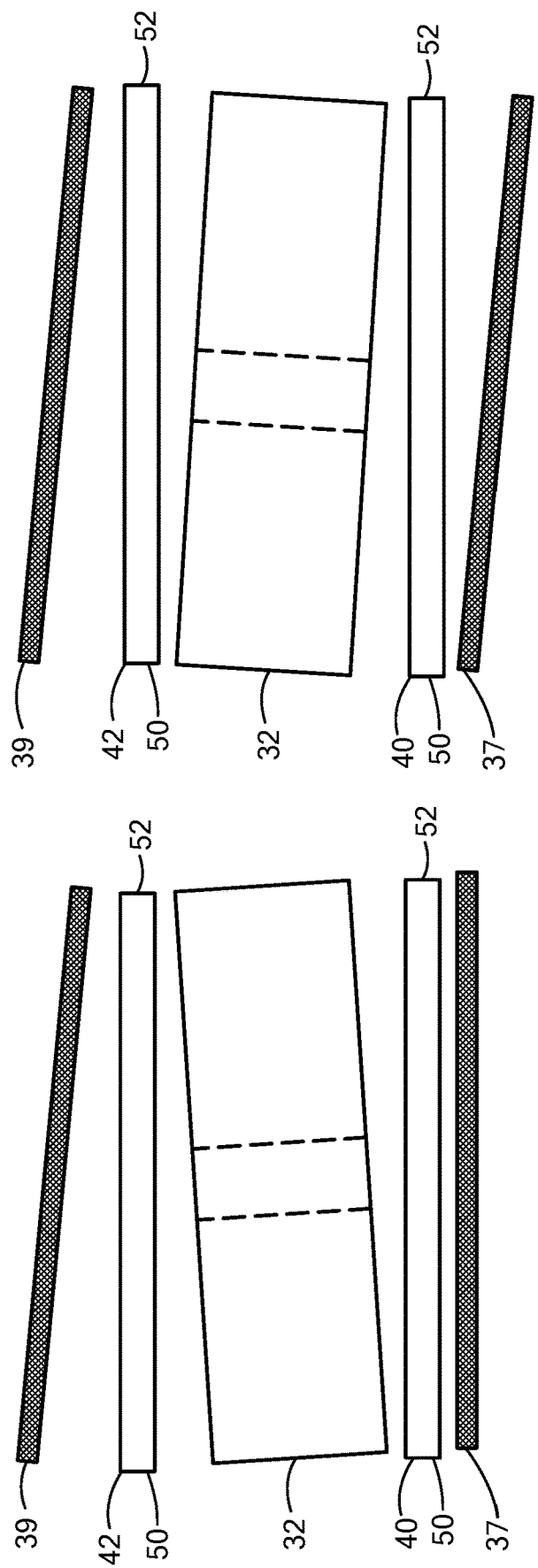

HVAD RINSE VIA A NON-UNIFORM THRUST BEARING GAP

CROSS-REFERENCE TO RELATED APPLICATION

This application claims the benefit of U.S. Application Ser. No. 62/811,618, filed Feb. 28, 2019.

FIELD

The present technology is generally related to implantable blood pumps.

BACKGROUND

Implantable blood pumps are commonly used to assist the pumping action of a failing heart. Typically, the implantable blood pump is surgically implanted in the patient's body and includes a housing with an inlet and an outlet and has a rotor mounted within the housing. The inlet of the housing is connected to a chamber of the patient's heart, typically the left ventricle, whereas the outlet is connected to an artery such as the aorta. Rotation of the pump's rotor drives the blood from the inlet towards the outlet and thus assists flow from the chamber of the heart into the artery.

Some implantable blood pumps are provided with contactless bearings so that, in operation, the rotor floats within the housing. With contactless bearings, there is no solid-to-solid contact between the rotor and the housing and thus no mechanical wear during operation. One form of contactless bearing is a hydrodynamic bearing. In a hydrodynamic bearing, the liquid being pumped passes between a surface of the rotor and a surface of the clearance between the surfaces of a hydrodynamic bearing is many times larger than the dimensions of blood cells. However, in some cases the blood passing through the pump may contain particles of thrombus, a solid or semi-solid deposit generated within the patient's body. The thrombus can lodge on a surface of the hydrodynamic bearing and impede its operation. The surfaces are configured so that as the rotor turns, the fluid disposed between these surfaces exerts pressure on the surface of the rotor that holds the rotor away from the housing.

SUMMARY

The techniques of this disclosure generally relate to an implantable centrifugal blood pump having a non-uniform thrust bearing gap.

In one aspect, the present disclosure provides for a blood pump having a housing including an inlet element. The inlet element has a proximal portion sized to be received within at least a portion of a heart of a patient and defines a major longitudinal axis. A rotor is configured to rotate within the housing about the major longitudinal axis and impel blood from heart. At least one stator is disposed within the housing and positioned within the housing at least one from the group consisting of upstream and downstream from the rotor. During operation of the blood pump the rotor is maintained at an oblique angle with respect to the major longitudinal axis.

In another aspect, the oblique angle is between 1-30 degrees from a longitudinal axis transverse to the major longitudinal axis.

In another aspect, the at least one stator includes a first stator downstream from the rotor and a second stator upstream from the rotor.

In another aspect, a first non-ferromagnetic disk is disposed between the first stator and the rotor and a second non-ferromagnetic disk is disposed between the second stator and the rotor.

In another aspect, the first stator includes a first back iron and the second stator includes a second back iron, and wherein at least one from the group consisting of the first back iron and the second back iron is disposed at an oblique angle with respect to the respective one of the first non-ferromagnetic disk and the second ferromagnetic disk.

In another aspect, the first back iron is disposed at an oblique angle with respect to the first non-ferromagnetic disk and the second back iron is disposed at an oblique angle with respect to the second ferromagnetic disk.

In another aspect, the oblique angle of the first back iron is the same as the oblique angle of the second back iron.

In another aspect, the rotor is an impeller, and wherein the impeller defines a plurality of hydrodynamic thrust bearings, and wherein the plurality of hydrodynamic thrust bearings face the second non-ferromagnetic disk.

In another aspect, the housing includes a center post, and wherein the rotor defines an opening sized to receive the center post, and wherein rotor rotates about the center post.

In another aspect, the center post includes a plurality of inner bearing magnets and wherein the rotor includes a plurality of outer bearing magnets, and wherein the plurality of inner bearing magnets and the plurality of outer bearing magnetics are configured to space the rotor a distance away from the center post, and wherein the plurality of inner bearing magnets are disposed at the oblique angle with respect the plurality of outer bearing magnets to cause the rotor to tilt at an oblique angle with respect to the major longitudinal axis.

In another aspect, the center post is symmetric about the major longitudinal axis.

In one aspect, the disclosure provides for a method of operating an implantable blood pump. The implantable blood pump includes an inflow cannula defining a major longitudinal axis and a rotor configured to rotate about the major longitudinal axis and impel blood downstream from the inflow cannula to an outlet downstream of the rotor. The method includes maintaining the impeller at a predetermined oblique angle with respect to the major longitudinal axis as it rotates about the major longitudinal axis.

In another aspect, the implantable blood pump is a centrifugal blood pump.

In another aspect, the oblique angle is between 1-30 degrees.

In another aspect, the implantable blood pump includes a stator having a back iron, and wherein the back iron is disposed at an oblique angle with respect to the major longitudinal axis.

In another aspect, the implantable blood pump includes a center post, and wherein the center post is disposed at an oblique angle with respect to the major longitudinal axis.

In another aspect, the implantable blood pump includes a center post, and wherein the center post includes a plurality of inner bearing magnets, and wherein the inner bearing magnets are disposed at an oblique angle with respect to the major longitudinal axis.

In another aspect, the implantable blood pump includes a stator having a back iron and a non-ferromagnetic disk disposed between the rotor and the stator, the back iron being spaced apart from non-ferromagnetic disk the and being disposed at an oblique angle with respect to the non-ferromagnetic disk.

In another aspect, the implantable blood pump includes a second stator having a second back iron and a second non-ferromagnetic disk disposed between the rotor and the second stator, the second back iron being spaced apart from second non-ferromagnetic disk the and being disposed at an oblique angle with respect to the second non-ferromagnetic disk.

In one aspect, the disclosure provides for a blood pump. The blood pump includes a housing including an inlet element, the inlet element having a proximal portion sized to be received within at least a portion of a heart of a patient and defining a major longitudinal axis. A rotor is configured to rotate within the housing about the major longitudinal axis and impel blood from heart. A first stator is disposed within the housing positioned downstream from the rotor and a second stator positioned within the housing positioned upstream from the rotor. A first non-ferromagnetic disk is disposed between the first stator and the rotor. During operation of the blood pump, the rotor is maintained at a predetermined and constant non-uniform distance from the first non-ferromagnetic disk.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3 is cross-sectional view of the impeller, first and second non-ferromagnetic disks, and first and second back-irons of the implantable blood pump shown in FIG. 2;

FIG. 4 is the impeller, first and second non-ferromagnetic disks, and first and second back-irons of the implantable blood pump shown in FIG. 3, with the first and second back-irons tilted at an oblique angle.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
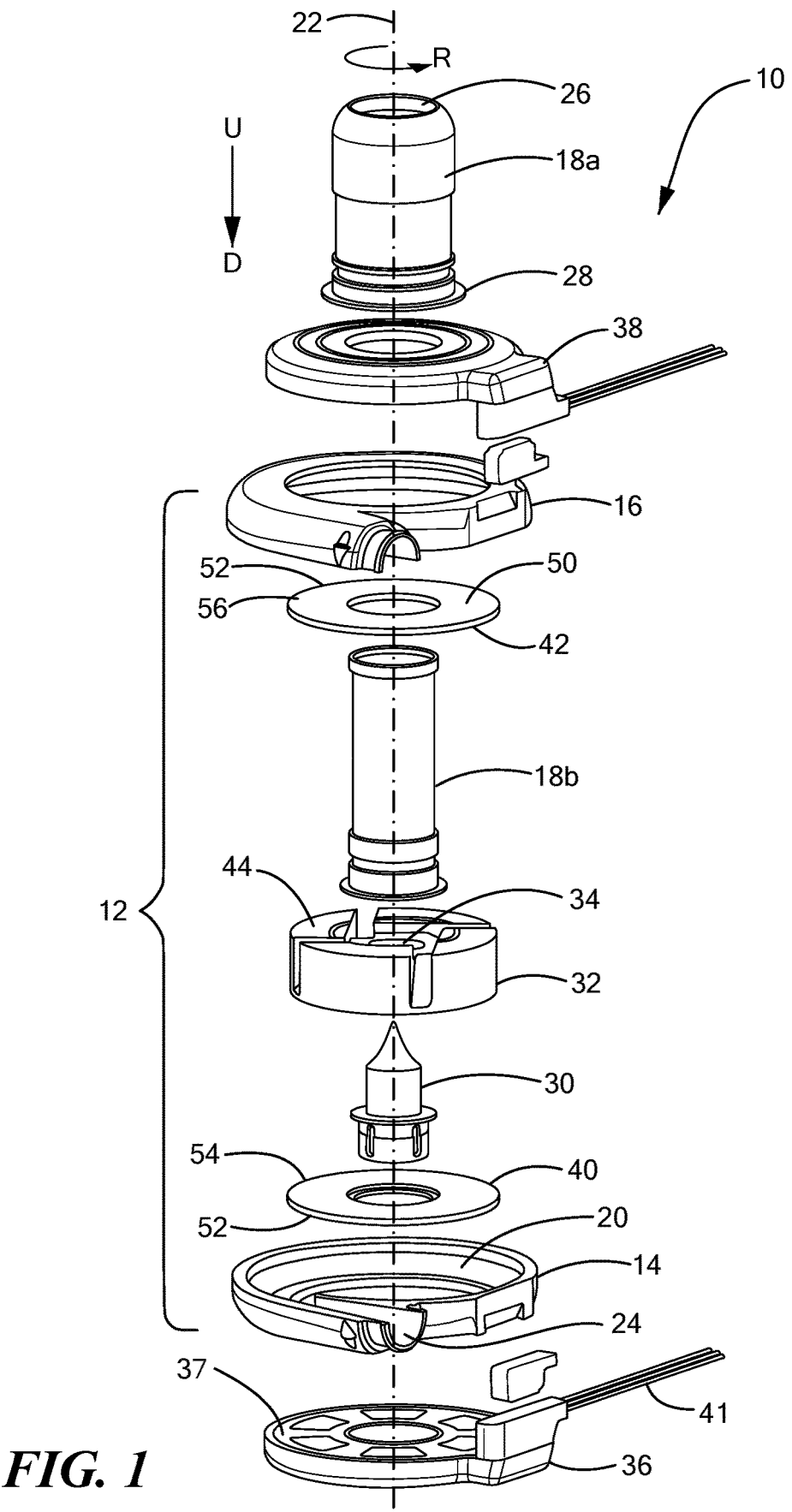
FIG. 1 is an exploded view of an implantable blood pump constructed in accordance with the principles of the present application.
Figure 2:
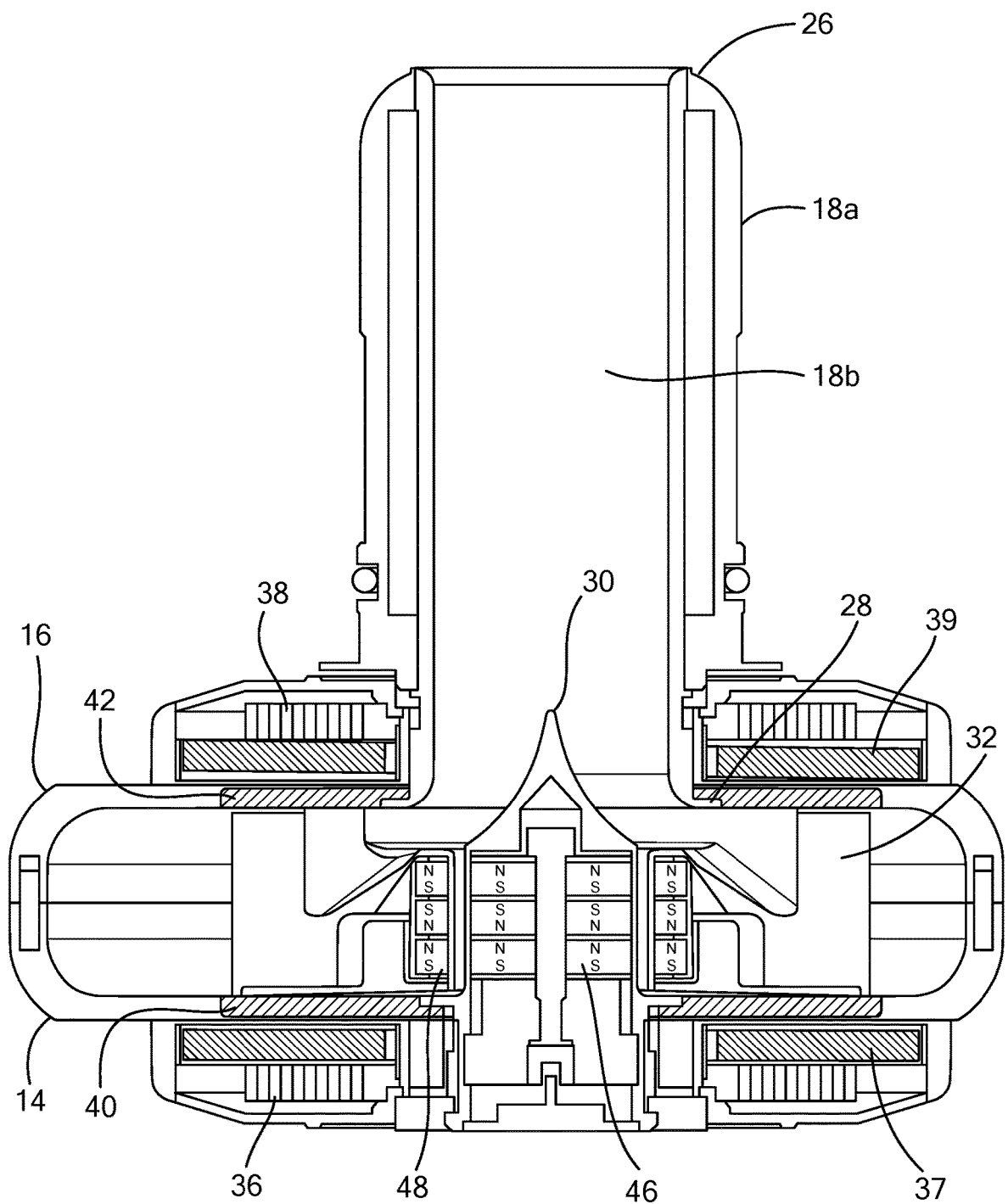
FIG. 2 is an assembled cross-sectional view of the implantable blood pump shown in FIG. 1 showing the magnetic polarities of the inner and outer bearings of the implantable blood pump and showing the second back-iron tilted.

Referring now to the drawings in which like reference designators refer to like elements there is shown in FIGS. 1-2 an exemplary blood pump constructed in accordance with the principles of the present application and designated generally "10." The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet element or inflow cannula 18 which includes an outer tube 18a and an inner tube 18b. The first portion 14 and the second portion 16 cooperatively define a volute-shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

The inflow cannula 18 is generally cylindrical and extends from second portion 16 generally along the axis 22. The inflow cannula 18 has an upstream end or proximal end 26 remote from the second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated in FIG. 1 by the arrows U and D respectively. A center post 30 is mounted to first portion 14 along and symmetric about axis 22. A generally disc-shaped ferromagnetic rotor or impeller 32 with a central hole 34 is mounted within chamber 20 for rotation about the axis 22. The rotor 32 includes a permanent magnet and flow channels for transferring blood from adjacent the center of the rotor 32 to the periphery of the rotor 32. In the assembled condition, the post 30 is received in the central hole of the rotor 32. A first stator 36 having at least two coils a first back iron 37 may be disposed within the first portion 14 downstream from the rotor 32. The first stator 36 may be axially aligned with the rotor along the axis 22 such that when a current is applied to the coils in the first stator 36, the electromagnetic forces generated by the first stator 36 rotate the rotor 32 and pump blood. A second stator 38 including a second back iron 39 may be disposed within the second portion 16 upstream from the rotor 32. The second stator 38 may be configured to operate in conjunction with or independently of the first stator 36 to rotate the rotor 32.

Electrical connectors 41 and 43 are provided on first portion 14 and second portion 16 respectively, for connecting the coils to a source of power such as a controller (not shown). The controller is arranged to apply power to the coils of the pump to create a rotating magnetic field which spins rotor 32 around axis 22 in a predetermined first direction of rotation, such as the direction R indicated by the arrow in FIG. 1, that is, counterclockwise as seen from the upstream end of inflow cannula 18. In other configurations of the blood pump 10, the first direction may be clockwise. Rotation of the rotor 32 impels blood downstream along the flow path so that the blood, moves in a downstream direction D along the flow path, and exits through the outlet 24. A first non-ferromagnetic disk 40, for example a ceramic disk, may be disposed within the first portion 14 downstream from the rotor 32 between the first stator 36 and the rotor 32. A second non-ferromagnetic disk 42 may be disposed upstream from the rotor 32 within the second portion 16 between the second stator 38 and the rotor 32. The first and second disks 40 and 42 may be composed of a ceramic material which is attached to the first portion 14 or the second portion 16 of the housing 12. During rotation, hydrodynamic bearings 44 and a plurality of inner magnetic bearings 46 and a plurality of outer magnetic bearings 48 support the rotor 32 and maintain the rotor 32 out of contact with the inner surfaces of the first non-ferromagnetic disk 40 and the second non-ferromagnetic disk 42. In other words, the operation of the rotor 32 is contactless in that it does not contact any component of the pump 10 other than fluid flowing through the pump 10. The general arrangement of the components described above may be similar to the blood pump 10 sold under the designation HVAD® by HeartWare, Inc., assignee of the present application. The arrangement of components such as the magnets, electromagnetic coils, and hydrodynamic bearings used in such a pump and variants of the same general design are generally described in U.S. Pat. Nos. 6,688,861; 7,575,423; 7,976,271; and 8,419,609, the disclosures of which are hereby incorporated by reference.

Referring now to FIGS. 2-3, in one configuration, during operation of the pump 10, the rotor 32 is maintained at an oblique angle with respect to the major longitudinal axis 22. For example, the rotor 32 may be tilted with respect to the major longitudinal axis 22 such that a gap between at least one from the group consisting of the first non-ferromagnetic disk 40 and the second non-ferromagnetic disk 42 is maintained at a predetermined non-uniform distance. In particular, as shown in FIG. 3, the rotor 32 has a smaller gap between the first non-ferromagnetic disk 42 toward a first hemisphere 50 of the first non-ferromagnetic disk 42 and a larger gap toward a second hemisphere 52 of the first non-ferromagnetic disk 42 opposite the first hemisphere 50. This gap is maintained as the rotor 32 rotates about the axis 22, as explained in more detail below, which may provide a gap through which thrombus can escape to avoid clotting or otherwise being deposited on the rotor 32.

In one configuration, to achieve and maintain the tilt of the rotor 32 at an oblique angle, which may be, for example, between 0.1-30 degrees, or any oblique angle, the second back iron 39 of second stator 38 may be angled with respect to the second non-ferromagnetic disk 42. In the example shown in FIG. 3, the second back-iron 39 is angled at an oblique angle which causes the rotor 32 to be tilted at an opposite oblique angle. In other words, the second back-iron 39 is angled so that it is closer to the second hemisphere 52 of the second non-ferromagnetic disk 42 than the first hemisphere 50. In such a configuration, the portion of the second back-iron that is closer to the rotor 32 exhibits a greater pull on the rotor 32 than compared to the portion of the back-iron 39 farther away from the rotor 32. During operation, the hydrodynamic thrust bearings 44 push the rotor 32 away from the second non-ferromagnetic disk 42 and counteract the pulling force of second back iron 39, thus the gap between the second non-ferromagnetic disk 42 and the second stator 38 is greater where the second back-iron 39 exerts less of a pulling force and the gap is maintained at this non-uniform distance.

In another configuration, as shown in FIG. 4, both the second back-iron 39 and the first back-iron 37 are tilted at the same or substantially the same oblique angles, which may be between 0.1-30 degrees, with respect to their respective non-ferromagnetic disks 40 and 42. The effect of both back irons 37 and 39 being tilted is to cause the rotor 32 to tilt at the same or substantially the same oblique angle as that of the back irons 37 and 39. In particular, as with the configuration shown in FIG. 3, the second back-iron 39 is closer to the second hemisphere 52 of the second non-ferromagnetic disk 42 compared to the first hemisphere 50 of the second non-ferromagnetic disk 42, whereas the first back-iron 39 is closer to the first hemisphere 50 of the first non-ferromagnetic disk 4 compared to the second hemisphere 52 of the second non-ferromagnetic disk 42. The tilt of the rotor 32 in this configuration may also be maintained at this non-uniform oblique angle during operation.

Figure 5:
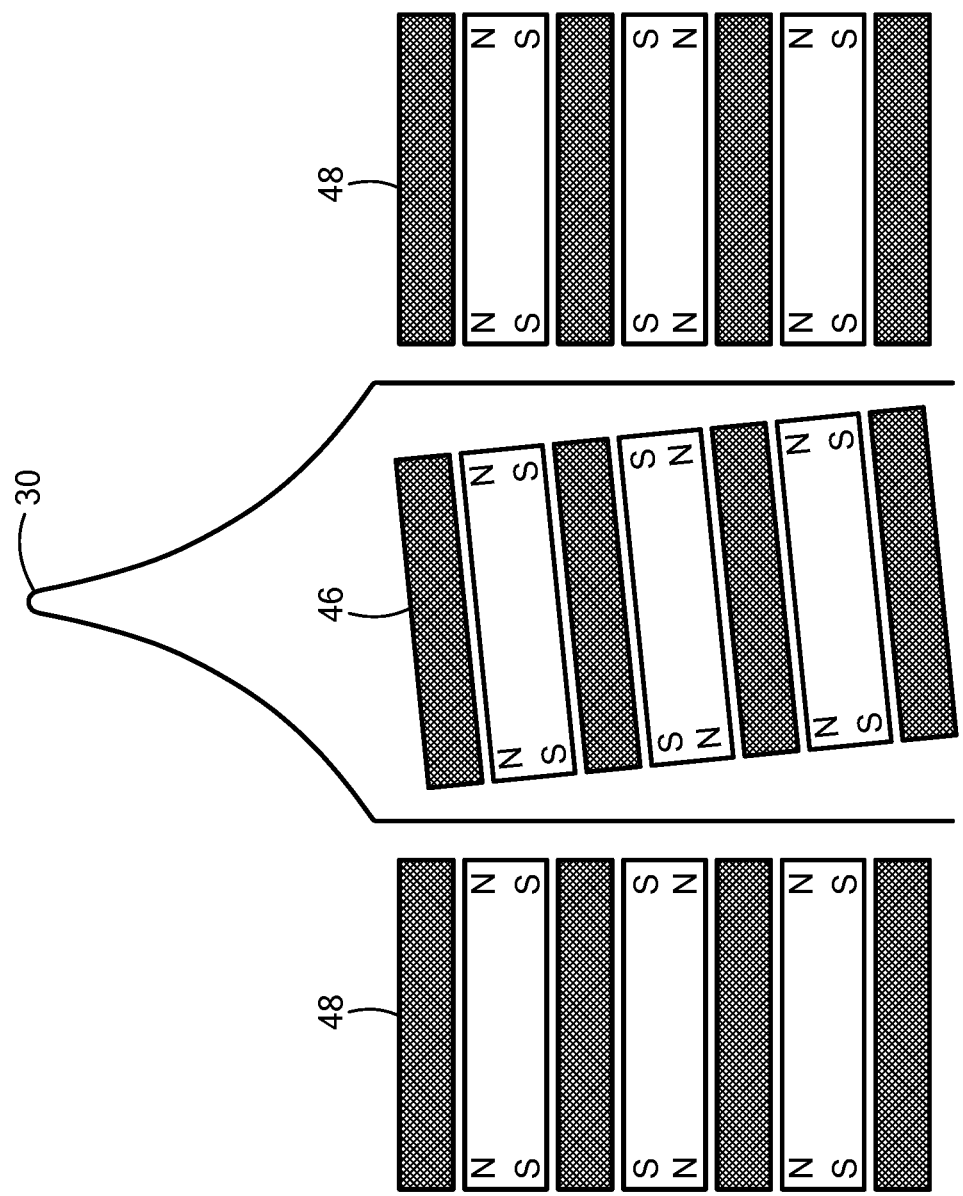
FIG. 5 is a cross-sectional view of an alternative embodiment of the inner and outer bearings shown in FIG. 2, in which the inner bearing is tilted at an oblique angle.

Referring now to FIG. 5, in another configuration, the inner bearing magnets 46 may be arranged or otherwise disposed within the center post 30 at an oblique angle with respect to the major longitudinal axis of the pump 10. In this configuration, the center post 30 is aligned and symmetric with the major longitudinal axis 22. Although not shown to scale in FIG. 5, the outer bearing magnets 48 of the rotor 32 may tilt in the same direction as the tilt of the inner bearing magnets 46 owing to the respective magnetic polarities. For example, in the configuration shown in FIG. 5, the outer bearing magnets 48 may tilt in the same direction as the tilt of the inner bearing magnets 46. The configuration shown in FIG. 5 may be combined with the configurations shown in either FIG. 3 or FIG. 4 or may alternatively be disposed in pumps having back irons with no tilt with respect to the major longitudinal axis.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A blood pump, comprising:
a housing including an inlet element, the inlet element having a proximal portion sized to be received within at least a portion of a heart of a patient and defining a major longitudinal axis;
a rotor configured to rotate within the housing via a contactless bearing and impel blood from heart; and
at least one stator disposed within the housing and positioned within the housing at least one of upstream or downstream from the rotor,
wherein during operation of the blood pump, the rotor is configured to rotate within the housing while tilted at an oblique angle with respect to the major longitudinal axis.

2. The pump of claim 1, wherein the oblique angle is between 1-30 degrees from a longitudinal axis transverse to the major longitudinal axis.

3. The pump of claim 1, wherein the at least one stator includes a first stator downstream from the rotor and a second stator upstream from the rotor.

4. The pump of claim 3, further including a first non-ferromagnetic disk disposed between the first stator and the rotor and a second non-ferromagnetic disk disposed between the second stator and the rotor.

5. The pump of claim 4, wherein the first stator includes a first back iron and the second stator includes a second back iron, and wherein at least one of the first back iron or the second back iron is disposed at an oblique angle with respect to the respective one of the first non-ferromagnetic disk or the second ferromagnetic disk.

6. The pump of claim 5, wherein the first back iron is disposed at an oblique angle with respect to the first non-ferromagnetic disk and the second back iron is disposed at an oblique angle with respect to the second ferromagnetic disk.

7. The pump of claim 6, wherein the oblique angle of the first back iron is the same as the oblique angle of the second back iron.

8. The pump of claim 5, wherein the rotor is an impeller, and wherein the impeller defines a plurality of hydrodynamic thrust bearings, and wherein the plurality of hydrodynamic thrust bearings face the second non-ferromagnetic disk.

9. The pump of claim 1, wherein the housing includes a center post, and wherein the rotor defines an opening sized to receive the center post, and wherein rotor rotates about the center post.

10. The pump of claim 9, wherein the center post includes a plurality of inner bearing magnets and wherein the rotor includes a plurality of outer bearing magnets, and wherein the plurality of inner bearing magnets and the plurality of outer bearing magnetics are configured to space the rotor a distance away from the center post, and wherein the plurality of inner bearing magnets are disposed at the oblique angle with respect the plurality of outer bearing magnets to cause the rotor to tilt at the oblique angle with respect to the major longitudinal axis.

11. The pump of claim 9, wherein the center post is symmetric about the major longitudinal axis.

12. A method comprising:
causing a rotor of an implantable blood pump to tilt at an oblique angle with respect to a major longitudinal axis defined by an inflow cannula of the implantable blood pump; and
rotating the rotor within a housing of the implantable blood pump while the rotor is tilted at the oblique angle, wherein the rotor is configured to contactlessly rotate within the housing.

13. The method of claim 12, wherein the implantable blood pump is a centrifugal blood pump.

14. The method of claim 12, wherein the oblique angle is between 1-30 degrees.

15. The method of claim 12, wherein the implantable blood pump includes a stator having a back iron, and wherein the back iron is disposed at an oblique angle with respect to the major longitudinal axis.

16. The method of claim 12, wherein the implantable blood pump includes a center post, and wherein the center post is disposed at an oblique angle with respect to the major longitudinal axis.

17. The method of claim 12, wherein the implantable blood pump includes a center post, and wherein the center post includes a plurality of inner bearing magnets, and wherein the inner bearing magnets are disposed at an oblique angle with respect to the major longitudinal axis.

18. The method of claim 12, wherein the implantable blood pump includes a stator having a back iron and a non-ferromagnetic disk disposed between the rotor and the stator, the back iron being spaced apart from non-ferromagnetic disk and being disposed at an oblique angle with respect to the non-ferromagnetic disk.

19. The method of claim 18, wherein the implantable blood pump includes a second stator having a second back iron and a second non-ferromagnetic disk disposed between the rotor and the second stator, the second back iron being spaced apart from the second non-ferromagnetic disk and being disposed at an oblique angle with respect to the second non-ferromagnetic disk.

20. A blood pump, comprising:
a housing including an inlet element, the inlet element having a proximal portion sized to be received within at least a portion of a heart of a patient and defining a major longitudinal axis;
a rotor configured to contactlessly rotate within the housing and impel blood from heart;
a first stator disposed within the housing positioned downstream from the rotor and a second stator positioned within the housing positioned upstream from the rotor; and
a first non-ferromagnetic disk disposed between the first stator and the rotor,
wherein, during operation of the blood pump, the rotor is configured to rotate within he housing while tilted at an oblique angle with respect to the major longitudinal axis and while maintained at a predetermined and constant non-uniform distance from the first non-ferromagnetic disk.

* * * * *